(12) United States Patent
Bertagnoli et al.

(10) Patent No.: US 7,547,309 B2
(45) Date of Patent: Jun. 16, 2009

(54) DISTRACTOR FOR LUMBAR INSERTION INSTRUMENT

(75) Inventors: Rudi Bertagnoli, Straubing (DE); Theirry Marnay, Castelnau le Lez (FR); Stephan Eckhof, Tuttlingen (DE); Christophe Geisert, Tuttlingen (DE); Eduard Kufeld, Tuttlingen (DE)

(73) Assignee: Spine Solutions, Inc., West Chester, PA (US)

( * ) Notice: Subject to any disclaimer, the term of this patent is extended or adjusted under 35 U.S.C. 154(b) by 531 days.

(21) Appl. No.: 10/947,660

(22) Filed: Sep. 23, 2004

(65) Prior Publication Data

US 2006/0064107 A1  Mar. 23, 2006

(51) Int. Cl.
*A61B 17/58* (2006.01)
(52) U.S. Cl. .................................................. 606/99
(58) Field of Classification Search ................ 606/99; 623/17.11, 17.14–17.16
See application file for complete search history.

(56) References Cited

U.S. PATENT DOCUMENTS

| | | | |
|---|---|---|---|
| 5,314,477 A | | 5/1994 | Marnay |
| 5,431,658 A * | | 7/1995 | Moskovich ............ 606/99 |
| 5,571,109 A | | 11/1996 | Bertagnoli |
| 6,159,215 A | | 12/2000 | Urbahns et al. |
| 6,224,599 B1 | | 5/2001 | Baynham et al. |
| 6,478,800 B1 | | 11/2002 | Fraser et al. |
| 6,565,574 B2 | | 5/2003 | Michelson |
| 6,599,294 B2 * | | 7/2003 | Fuss et al. ............ 606/99 |
| 6,610,065 B1 | | 8/2003 | Branch et al. |
| 6,652,533 B2 * | | 11/2003 | O'Neil ............ 606/100 |
| 6,755,841 B2 * | | 6/2004 | Fraser et al. ............ 606/99 |
| 7,118,580 B1 * | | 10/2006 | Beyersdorff et al. ...... 606/99 |
| 2003/0069586 A1 | | 4/2003 | Errico et al. |
| 2004/0030387 A1 * | | 2/2004 | Landry et al. ....... 623/16.11 |
| 2004/0143332 A1 * | | 7/2004 | Krueger et al. ........ 623/17.14 |
| 2004/0225295 A1 * | | 11/2004 | Zubok et al. ............ 606/90 |
| 2005/0228500 A1 * | | 10/2005 | Kim et al. ........... 623/17.13 |
| 2006/0030856 A1 * | | 2/2006 | Drewry et al. ........... 606/90 |
| 2006/0089656 A1 * | | 4/2006 | Allard et al. ............ 606/99 |
| 2006/0149273 A1 * | | 7/2006 | Ross et al. ............ 606/86 |
| 2006/0241641 A1 * | | 10/2006 | Albans et al. ........... 606/90 |

FOREIGN PATENT DOCUMENTS

| | | |
|---|---|---|
| WO | WO-01/01893 | 1/2001 |
| WO | WO-01/19295 | 3/2001 |

* cited by examiner

*Primary Examiner*—Eduardo C Robert
*Assistant Examiner*—Nicholas Woodall
(74) *Attorney, Agent, or Firm*—Woodcock Washburn LLP

(57) ABSTRACT

An instrument and method are disclosed for inserting an artificial intervertebral disc implant having upper and lower parts and a pivot element therebetween into an intervertebral space. The instrument has a mounting structure, and an elongated upper arm and elongated lower arms, the arms being pivotally attached to the mounting structure. A distractor separates the upper and lower arms, and hence the upper and lower parts, when moving along the arms so as to permit insertion of the pivot element. The distractor includes a fork arm that extends beyond a main body thereof to engage and support with heads thereof a facing surface of the upper and/or lower part during and following separation of the parts.

34 Claims, 10 Drawing Sheets

DISTRACTOR FOR LUMBAR INSERTION INSTRUMENT

FIELD OF THE INVENTION

This invention relates to instruments for inserting intervertebral implants, and more specifically to new and improved instruments and methods for inserting an artificial intervertebral disc implant into an intervertebral space.

BACKGROUND OF THE INVENTION

Currently, when it is necessary to completely remove a disc from between adjacent vertebrae, the conventional procedure is to fuse the adjacent vertebrae together. This "spinal fusion" procedure is a widely accepted surgical treatment for symptomatic lumbar degenerative disc disease. However, reported clinical results vary considerably, and complication rates are considered by some to be unacceptably high.

More recently, there have been important developments in the field of disc replacement, namely disc arthoplasty, which involves the insertion of an artificial intervertebral disc implant into the intervertebral space between adjacent vertebrae, and which allows limited universal movement of the adjacent vertebrae with respect to each other.

The aim of total disc replacement is to remove pain generation (disc), restore anatomy (disc height), and maintain mobility in the functional spinal unit so that the spine remains in an adapted sagittal balance. Sagittal balance is be defined as the equilibrium of the trunk with the legs and pelvis to maintain harmonious sagittal curves. In contrast with fusion techniques, total disc replacement preserves mobility in the motion segment and mimics physiologic conditions.

One such intervertebral implant includes an upper part, or upper plate, That can communicate with a vertebrae, a lower part, or lower plate that can Communicate with the adjacent vertebrae, and a pivot element, or third part, inserted between these two parts. An example of an instrument for this type of implant is disclosed in U.S. Pat. No. 5,314,477. More specifically, tongs are disclosed that can be used, after the insertion of the pivot element between the upper and lower parts of the implant, to move the two vertebrae apart to a distance sufficient for introducing the assembled implant into that space. Additionally, instruments exist for inserting intervertebral implants that move the implant along a longitudinal guide as far as the implant point, and then feed the implant out of the guide and into the intervertebral space. See U.S. Pat. No. 5,571,109. However, both of these instruments are suitable only for inserting complete implants.

An improved instrument is shown in Published Application No. WO 01/01893, published Jan. 11, 2001 and incorporated by reference, and instruments for inserting same are shown in Published Application No. WO 01/19295, published Mar. 22, 2001 and incorporated herein by reference. These applications disclose an arrangement wherein the upper and lower parts of the implant, without the pivot element, are inserted into the intervertebral space, after which the upper and lower parts are separated and the pivot element is inserted therebetween. The terms "separated" and "distracted" are used interchangeably and have the same meaning herein.

In particular, the instrument shown in Published Application No. WO 01/19295 includes: a) an upper arm for engaging an upper part of the implant, b) a lower arm for engaging a lower part of the implant, c) a separate distractor for separating the upper and lower parts from each other after they have been inserted into the intervertebral space, and d) a pusher element for pushing the pivot element along the length of the instrument between the two lower arms and directly into the lower part. After location of the pivot element, the distractor is retracted, allowing the two adjacent vertebrae to come together which urges the upper and lower parts together against the pivot element.

While these and other known instruments and methods represent improvements in the art of artificial intervertebral implant insertion, there exists a continuing need in the art for improvements in the field of instruments and methods for inserting intervertebral implants.

BRIEF SUMMARY OF THE INVENTION

A purpose of the present invention is to provide a new and improved instrument and method for inserting an intervertebral disc implant.

The instruments and methods of the present invention are used to insert various sized artificial intervertebral disc implants at any location along the spine, including especially the lumbar and cervical spine.

An intervertebral implant is normally inserted anteriorly, i.e., from the patient's anterior moving towards the patient's posterior. However, it is to be understood that the implant, the instruments and a method can also be designed and arranged to insert the implant laterally, i.e., from the side or obliquely, from the side-front. To avoid confusion with respect to the patient's anatomy, the invention will be described herein with respect to more simple terminology which relates to instruments and methods themselves. For example, in describing the invention, the terms "front" or "forward" mean the part of the instrument which faces toward the vertebrae or is moving in the direction of movement toward the vertebrae, and the words "back", "rear", or "rearward" refer to the end of the instrument furthest from the vertebrae or moving away from the vertebrae. Also, in this application, the words "upper", "lower", "uppermost" or "lowermost" or any other words describing orientation of the intervertebral implant or the instruments or methods associated therewith are used only for convenience and are not intended to convey any limitation. More specifically, the parts of the implant, the instrument and/or the methods described in this application with reference to the upper part or plate can in fact be positioned as the superior or inferior part within the patient's vertebrae, with the other of the two parts being the opposite part.

The instrument and the method of the present invention are particularly adapted for use with an artificial intervertebral disc implant having upper and lower parts which undergo limited universal movement with respect to each other, with the upper and lower surfaces of the upper and lower parts engaging the adjacent vertebral surfaces.

For example, the instrument and method of the present invention are used in connection with implant devices that have an upper part or plate and a lower part or plate, and a pivot element therebetween.

In the prior arrangement of WO 01/19295, it has been noted that support of the upper part during a high force distracting movement is not easy. Specifically, in this prior arrangement, the sole engagement of the arms with their respective parts are by way of pins at the end of each of the upper and lower arms engaging apertures in the front of the upper and lower parts. During the exertion of high forces by the distractor to move the upper and lower parts apart, and hence the adjacent vertebrae apart, the posterior portion of the upper part farthest from its engaging pins would have a tendency to move (pivot) into the newly created space.

The present invention improves upon the previous instrument by providing a new and improved distractor element which is constructed and arranged such that it moves the upper and lower parts apart, and hence the adjacent vertebrae, apart. This distractor has a new forward end, or forward arm, which engages and at least supports the upper part along at least the posterior portion thereof, by extending into the space between the upper and lower parts and engaging the interior lower surface of the upper part.

In a preferred arrangement, this forward end of the distractor comprises a pair of fork arms which extend along the bottom of the upper part, offset to one side or the other so as not to interfere with a central portion of the upper part which forms a surface for receiving the pivot element. It will be appreciated that the upper part is always finally engaged at least at the posterior portion thereof by a respective head of each fork arm.

Thus, it is an object of the present invention to provide a new and improved instrument for distracting upper and lower parts of an intervertebral disc implant.

It is another object of the present invention to provide a new and improved method for separating the upper and lower parts of an intervertebral disc implant.

These and other objects of the present invention will become apparent from the detailed description to follow, together with the accompanying drawings.

BRIEF DESCRIPTION OF THE DRAWINGS

Embodiments of the present invention will now be discussed by way of example with reference to the drawings. It is emphasized that these drawings are exemplary in nature and are not to be construed as limiting the present invention.

DETAILED DESCRIPTION OF THE PREFERRED EMBODIMENTS

Figure 1:
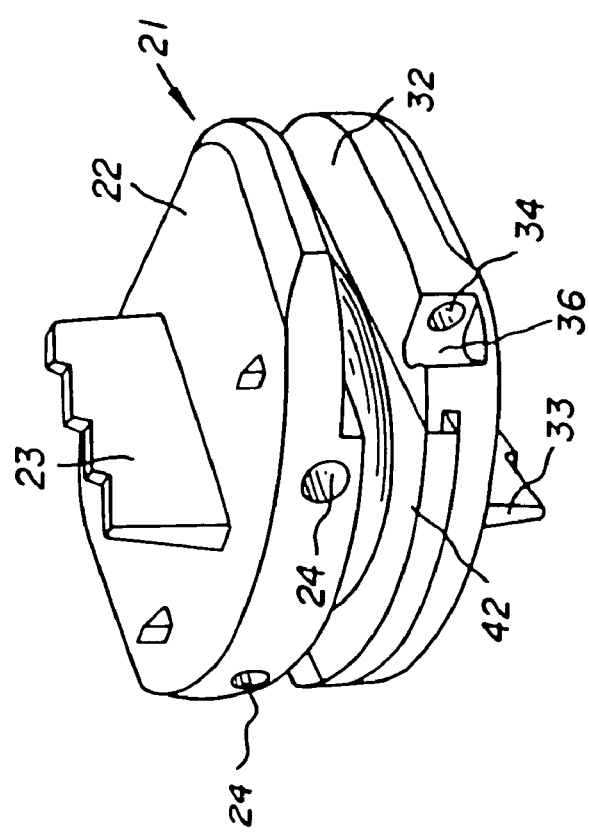
FIG. 1 is a perspective view of one prior art type of intervertebral implant for use with the instruments and method of the present invention.

Referring now to the drawings, like elements are represented by like numerals throughout the several views. As stated above, embodiments of the present invention are directed to instruments and methods for inserting artificial intervertebral disc implants 21 or the like. As known in the art, prior to inserting of an intervertebral disc implant 21, the intervertebral space must be cleaned out with instruments such as elevators and/or chisels. After the intervertebral space has been cleaned out in preparation for receiving intervertebral disc implant 21, the next step is to determine the precise size of an inlay protrusion 44 of a pivot element 42 (which is located between an upper part 22 and a lower part 32 of implant 21) which provides a correct overall height for disc implant 21 for that particular (height) intervertebral space. This determination is accomplished by providing a set of trial implants of different sizes. The operator thus selects by experience the trial implant that the operator believes would be the most appropriate for that particular intervertebral space and disc implant 21 selected.

Once the correct trial implant has been selected, the next step is to form the cutouts in the adjacent vertebrae using the trial implant. These cutouts are designed to receive raised keels of the upper and lower plates. Typically, a chisel is used to form the required cutouts in the opposed vertebrae. In accordance with the present invention, an insertion instrument 50 disclosed hereafter is then used to insert intervertebral implant 21 into the intervertebral space defined by the two vertebrae as explained in detail below.

Figure 2:
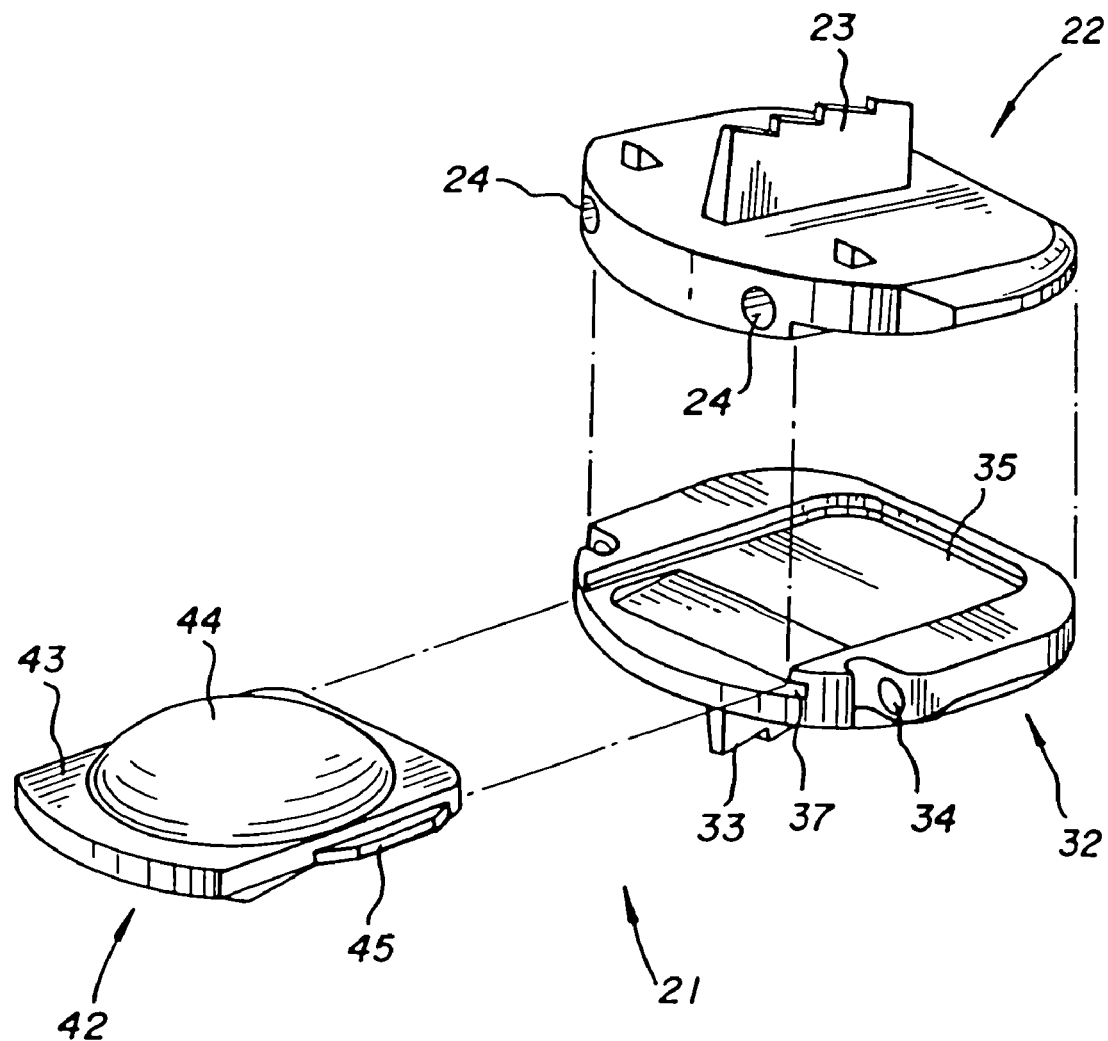
FIG. 2 is an exploded perspective view of an upper plate, a pivot element and a lower plate of the intervertebral implant depicted in FIG. 1.
Figure 10:
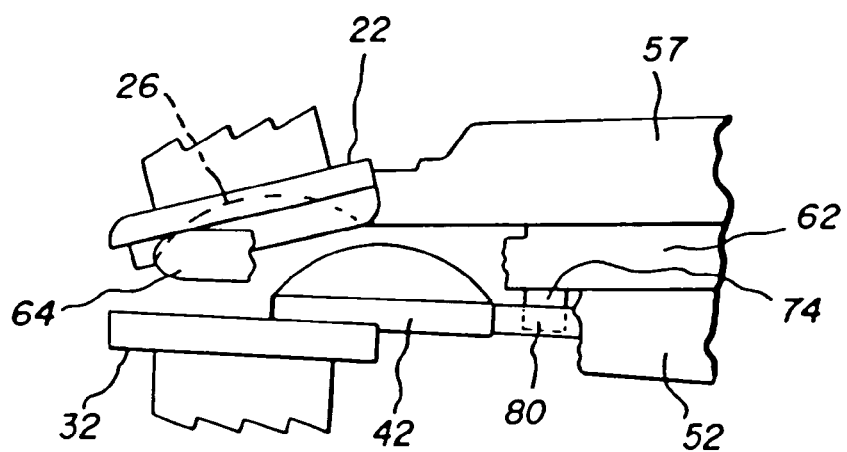
FIG. 10 is a side elevational view of the introduction space created by the insertion instrument.
Figure 11:
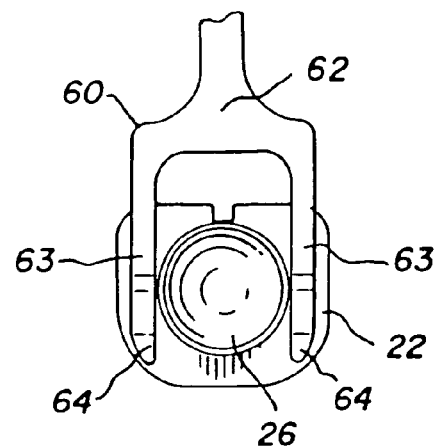
FIG. 11 a bottom view of the upper part and associated fork arms in the position depicted in FIG. 10.

Typically, examples of intervertebral disc implants 21 used in connection with the present invention will include those similar to disc implant 21 depicted in detail in FIGS. 1-2. FIGS. 1-2 show disc implant 21 having upper part 22 with a raised keel 23 protruding therefrom, and lower part 32 with a raised keel 33 protruding therefrom. Also shown are upper insertion apertures 24 and one of two lower apertures 34. Pivot element 42 is shown in place between upper part 22 and lower part 32 in FIGS. 1 and 2, and in a position to be inserted into the holding space of the lower part 32 in FIG. 2. Upper part 22 (as shown in FIGS. 10 and 11) has a domed-shaped concave bearing face 26 which receives a mating convex inlay protrusion 44 of pivot element 42.

Pivot element 42, shown best in FIG. 2, will typically have a substantially rectangular base 43 which is to be captured in a recess 35 of lower part 32 and protrusion 44 which is to be received in concave domed-shaped bearing face 26 of upper part 22. Lower part 32, shown best in FIG. 2, comprises a recess 35 to snugly receive rectangular base 43 of pivot element 42. Pivot element 42 can be inserted into recess 35 from the open side as shown in FIG. 2, allowing opposite edges 45 of base 43 to engage lateral grooves 37 in lower part 32 so that pivot element 42 can be inserted and then moved forwardly along grooves 37 into a fully inserted/captured position in recess 35. Other details of implant 21 are disclosed in WO 01/01893 as noted above and thus need not be discussed here further.

When implanted, as also fully disclosed in WO 01/01893, inlay protrusion 44 engages concave bearing face 26 of upper part 22, so that upper part 22 and lower part 32 are braced on one another via pivot element 42 and have a pivotal relationship one to the other. Both upper part 22 and lower part 32 on a front or anterior face thereof have insertion apertures 24, 34 which are designed to receive mounting pins 51 of the insertion instrument of the present invention as described below. FIG. 1 clearly shows upper part 22 and lower part 32 with pivot element 42 positioned therebetween so that relative pivoting of upper part 22 and lower part 32 is permitted.

Figure 3:
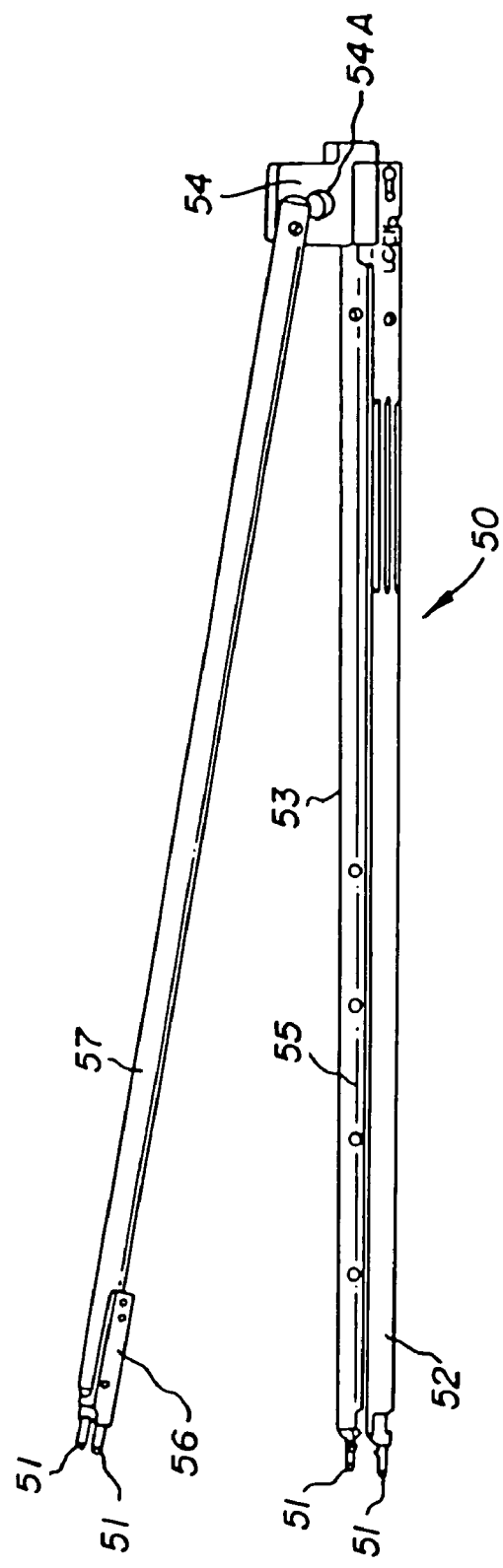
FIG. 3 is a perspective view of a partially assembled insertion instrument of the present invention.

As shown in FIG. 3 and similar to the instrument disclosed in WO 01/01893, insertion instrument 50 of the present invention has an elongated upper arm 57 and substantially parallel elongated lower arms 52, 53. Upper arm 57 and lower arms 52, 53 engage a mounting structure 54, which holds the adjacent ends of arms 52, 53 and 57 as noted below. The second or free ends of lower arms 52, 53 are each engageable in lower part 32 of disc implant 21 while the second or free end of upper arm 57 is engageable in upper part 22. Referring to FIG. 3, these engagements are accomplished by retaining pins 51 on the associated ends of each arm 52, 53, 57. A holder 56 is used to attach pins 51 to upper arm 57 as broadly described in WO 01/19295, by which upper part 22 is engaged with upper arm 57 at a predetermined slight angle to vertical as shown. Mounting structure 54 includes an opening 54A with a spring-loaded ball catch (not shown) therein which receives mounting portion 66A of a part of the casing 66 (see FIG. 4) to secure the distractor, as discussed in detail below.

In the embodiments of the present invention, lower arms 52, 53 are rotatable about their central, longitudinal axes in order to lock lower arms 52, 53 to lower part 32 as shown and described in WO 01/19295 and as described below with respect to FIG. 5. As also described in WO 01/19295, upper arm 57 has pins 51 of holder 56 slidably received in apertures 24 of upper part 22 as shown in FIG. 6. However, in this embodiment it will be appreciated that holder 56 is rigid with upper arm 57 and hence does not pivot relative to upper arm 57 as does the holder disclosed in WO 01/19295.

As stated above, mounting structure 54 holds arms 52, 53, 57 in pivotable relationship with one another, with lower arms 52, 53 parallel to one another and with upper arm 57 at a small angle to the plane of lower arms 52, 53. In the embodiments of the present invention, mounting structure 54 is spaced apart from the plane defined by the two lower arms 52 and 53. Upper arm 57 is vertically disposed approximately midway between the two lower arms 52 and 53, so that the free or forward end of upper arm 57 can, in its lowered position, enter the space between the two parallel lower arms 52 and 53.

As shown in FIG. 6, upper arm 57 is circular in cross section and on its free end carries U-shaped holder 56 which receives the free end of upper arm 57. Holder 56 and upper arm 57 are immovably joined together as noted above.

Figure 4:
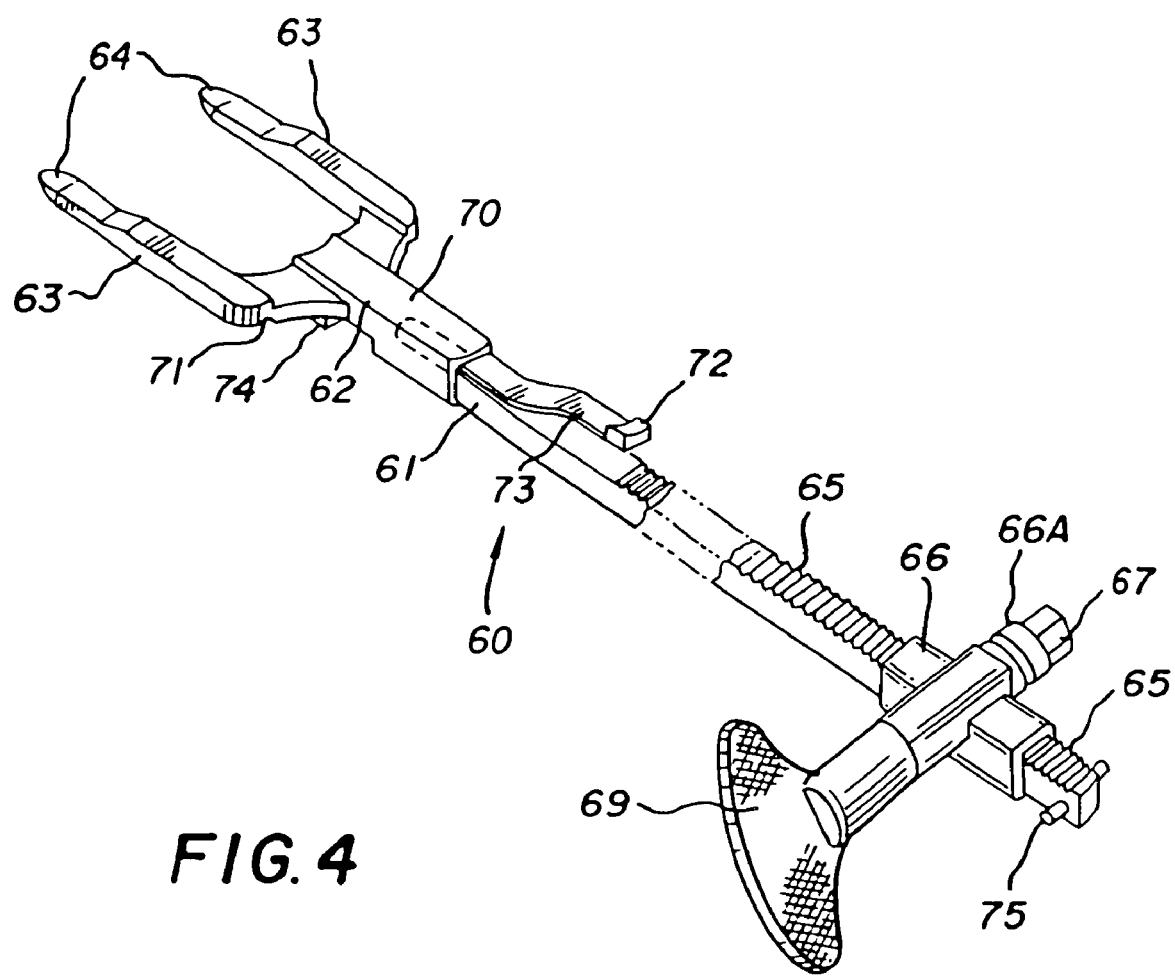
FIG. 4 is a perspective view of a fork distractor of the present invention.
Figure 7:
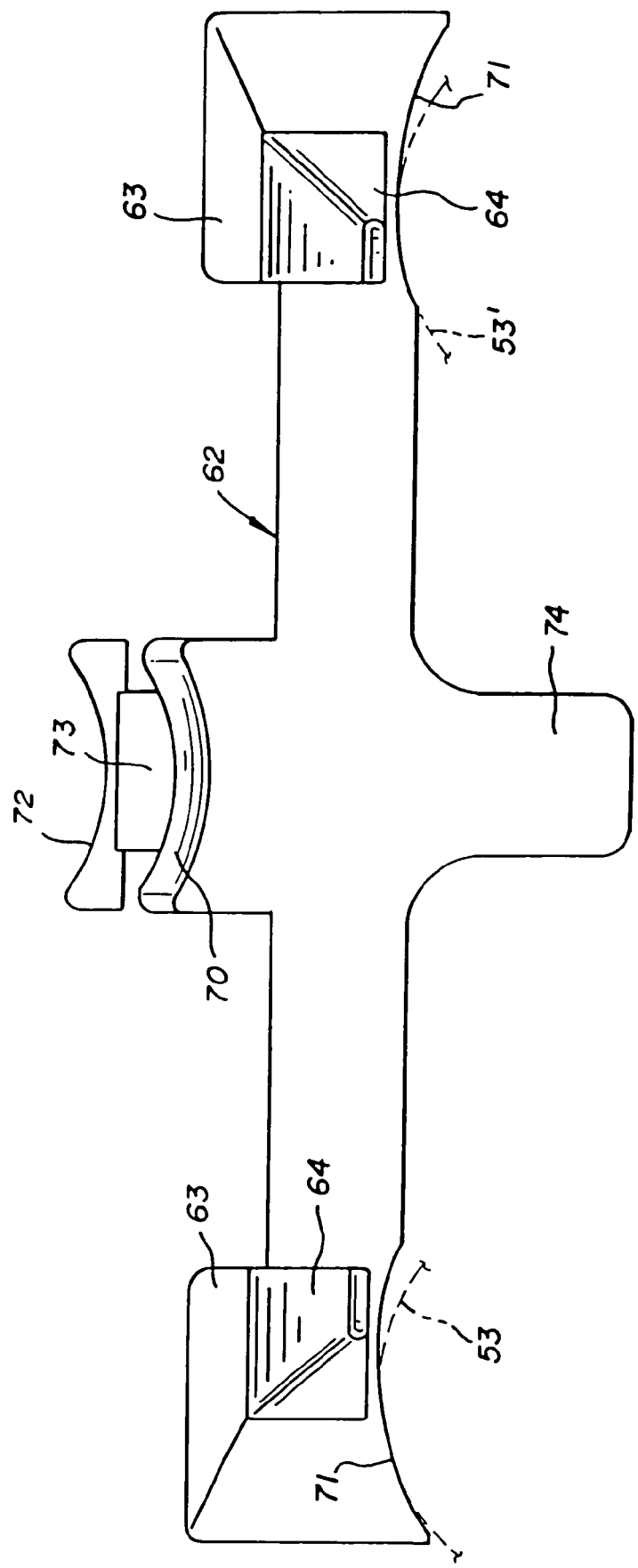
FIG. 7 is an enlarged front view of the body of the fork distractor of the present invention.

Instrument 50 of the present invention further comprises a distractor 60, as shown best in FIG. 4, which comprises an elongated arm 61 with a body 62 securely attached thereto. At a forward end of body 62 there are a pair of fork-shaped arms 63 that extend forward beyond body 62 substantially parallel to the longitudinal axis of arm 61. As shown in FIGS. 4 and 7, body 62 has a solid wedge portion 70 which matingly seats with and engages upper arm 57 as wedge portion 70 approaches the free end of upper arm 57. In addition, as best shown in FIG. 7, fork arms 63 also have rounded lower seats 71 which similarly engage the adjacent portions of lower arms 52 and 53. It will be appreciated that distractor 60 is usable with instruments 50 having differently spaced lower arms 53. Thus, as shown in FIG. 7, the outside portion of seats 71 are designed to mate against lower arms 53 (only one of which is partially shown in phantom) where instrument 50 has widely spaced lower arms 53 (for larger sized implants 21); while the inside portion of seats 71 are similarly designed to mate against lower arms 53' (only one of which is partially shown in phantom) where instrument 50 has more closely spaced lower arms 53' (for smaller sized implants 21). If only one spacing of lower arms 50 is usable, then seats 71 can be designed to mate over the entire surface thereof with the associated lower arm 53.

As wedge portion 70 moves forward along arms 52, 53 and 57 and approaches disc implant 21, wedge portion 70 forces upper arm 57 slowly away from lower arms 52, 53, creating a small starting space between upper part 22 and lower part 32. It will thus be appreciated that wedge portion 70 serves a function similar to the spreader element (43) disclosed in WO 01/19295. It will also be appreciated that body 62 includes a protrusion 74 which also serves a function similar to protrusion 44 disclosed in WO 01/19295. In particular, protrusion 74 is used to initially push rectangular base 43 of pivot element 42—whose edges 45 engage longitudinal grooves 55 provided along opposing (facing) inner sides of lower arms 52, 53—forward to a position immediately adjacent implant 21 and then partially into recess 35. The final forward movement of pivot element 42 is then accomplished using a pushing element 80 (see FIG. 10) similar to that described in WO 01/19295, which also engages rectangular base 43 so that no potentially damaging contact is made with inlay protrusion 44.

It will also be appreciated that distractor 60 of the present invention may further include a leaf spring 73 provided behind wedge portion 70 which resiliently mounts a seat 72. When distractor 60 is first located between arms 52, 53 and 57 and body 62 is rearward or near mounting structure 54, seats 71 rest loosely on arms 52 and 53 but wedge portion 70 is too far away from upper arm 57 to have contact therewith (due to the angle of arm 57 to the plane of lower arms 52, 53). Thus, at this position it is seat 72 that resiliently engages arm 57 to gently hold body 62 in position between arms 52, 53 and 57 (working together with mounting structure 54 as explained below) to assure that protrusion 74 is in position to engage and hence move pivot element 42 forward along lower arms 52, 53 as body 62 is moved toward implant 21. Then, as distractor 60 moves along upper arm 57 and lower arms 52, 53 adjacent mounting structure 54 toward disc implant 21 at the forward end of arms 52, 53 and 57, the angle of upper arm 57 relative to lower arms 52, 53 gradually forces seat 72 down toward arm 61. This movement of seat 72 is made against the mild force of leaf spring 73, so that only a minor reactive force is exerted on arms 52, 53 and 57 which is insufficient to force upper part 22 and lower part 32 of disc implant 21 apart (so that no significant separating forces are conveyed to upper part 22 and lower part 32). It will be appreciated that seat 72 does not actually contact arm 61 during this movement, since wedge portion 70 is slightly higher than the thickness of seat 72 so that wedge portion 70 takes over the holding function of seat 72 when fork arms 63 approach implant 21—and turns this holding function additionally to a separating function as noted below.

Figure 8:
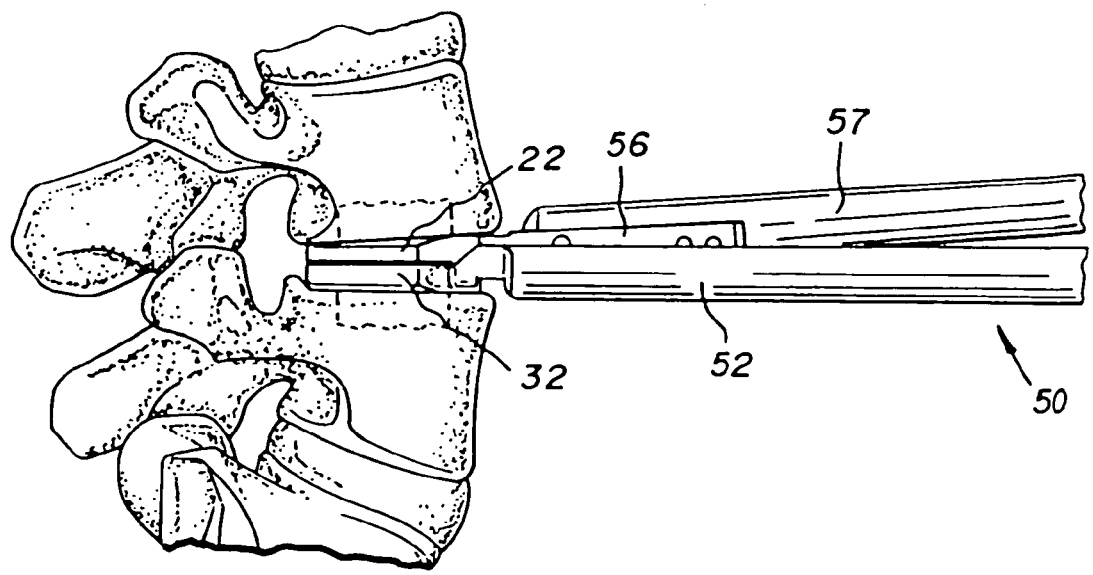
FIG. 8 is a side elevational view of an insertion instrument of the present invention engaged with the upper and lower parts of an intervertebral disc implant after insertion of the upper and lower parts of the implant into an intervertebral space.

Distractor 60 engages upper arm 57 and lower arms 52, 53 in such a way that as distractor 60 slides forward along between lower arms 52, 53 it rides along the top of lower arms 52, 53 and first seat 72 of leaf spring 73 engages upper arm 57 and then wedge portion 70 engages upper arm 57. FIG. 8 shows the position of the upper and lower parts 22, 32 nested together (as described in WO 01/19295) in their closed or initial position before wedge portion 70 (not shown in this Figure) engages upper arm 57 and lower arms 52, 53. With the parts in this position, distractor 60, as it moves further forward along upper arm 57 and lower arms 52, 53 towards disc implant 21, will slightly separate upper and lower parts 22, 32 from each other (and hence slightly enlarge the intervertebral space), as wedge portion 70 of distractor 60 urges upper arm 57 upwardly slightly, creating a starting space. This starting space is relatively easy to create, as the intervertebral forces holding upper part 22 and lower part 32 adjacent one another are initially small. When this starting space is created, it will be appreciated that protrusion 74 has caused pivot element 42 to be located immediately adjacent recess 35 and thus ready to be pushed forward into recess 35 as fork arms 63 move forward between upper part 22 and lower part 32 and wedge portion 70 and/or fork arms 63 open a space sufficient for receiving pivot element 42 to pass into (as discussed below).

In the prior art WO 01/19295, further wedging movement of the similar protrusion element was designed to effect a sufficient space so that pivot element 42 could be easily inserted partially onto lower part 32 using the protrusion without interference from upper part 22. However, as the force required to separate the upper part 22 from the lower part increased with the increased separation distance (the resistance of the forces trying to close the intervertebral space increased), it would not always be easy to achieve the required spacing and/or the desired orientation of upper part 22 relative to lower part 32 was not easily maintained.

In order to make this separation easier, in accordance with the present invention, after the starting space is provided by wedge portion 70, further advancement of distractor 60 causes fork arms 63 to enter the already created starting space. Entry of heads 64 of fork arms 63 into the staring space is facilitated by the tapered front end of each head 64. As the heads 64 of fork arms 63 enter the starting space between upper part 22 and lower part 32 and further forward movement of distractor 60 occurs, one or both of two reactive forces are exerted to positively force upper part 22 further away from lower part 32 in order to provide the needed spacing therebetween. The first force is that of wedge portion 70 acting on upper part 22, while the second force is that of heads 64 of fork arms 63. These forces act in concert in the following manners, which obviously depend on the relative sizes of wedge portion 70 and heads 64 of fork arms 63 (as discussed below with respect to FIGS. 13A-B) as well as the amount of pivoting into the separation space which the posterior end of upper part 22 experiences as distractor 60 moves forward.

Typically where there is only some resistance to the distracting movement of upper part 22 away from lower part 32, as where the intervertebral space receiving implant 21 is large so not much widening is needed, wedge portion 70 may be sufficient by itself to perform all or most of the needed distracting movement. In this case, heads 64 of fork arms 63 may provide no or only a minor effective distracting force. It will be appreciated that where fork arms 63 provide essentially no distracting force, heads 64 of fork arms 63 nonetheless will engage along upper part 22 and provide a holding or supporting force along upper part 22 to maintain upper part 22 in the proper orientation with lower part 32 (and hence to prevent falling or pivoting of upper part 22). Similarly, where heads 64 of fork arms 63 provide only a minor distracting force (which distracting force also serves to support or hold), this distracting force of heads 64 of fork arms 63 will primarily be exerted as heads 64 of fork arms 63 engage along upper part 22 as wedge portion 70 does not provide the complete distracting force necessary. Typically when either no distractor force (with supporting/holding occurring) or some distracting force is exerted by heads 64 of fork arms 63, heads 64 of fork arms 63 only begin to contact upper part 22 after passing some of the anterior portion thereof; but this supporting/holding/forcing could occur starting at the anterior portion, but more likely will occur starting near the posterior portion of upper part 22 at the end of the forward movement of distractor 60. In addition, heads 64 of fork arms 63 can begin providing only a supporting/holding force and then provide some distracting force, or vice versa or alternately, as forward movement of distractor 60 occurs.

Typically where there is significant resistance to the distracting movement of upper part 22 away from lower part 32, as where the intervertebral space receiving implant 21 is small so a more forceful widening may be needed, heads 64 of fork arms 63 may perform all or most of the distracting movement after the initial starting space at the anterior end of upper part 22 is created by wedge portion 70. In this case, wedge portion 70 may provide no or only a minor additional effective distracting force. It will be appreciated that where wedge portion 70 provides essentially no additional distracting force, wedge portion 70 may or will nonetheless provide a holding or supporting force at the anterior part of upper part 22 to help maintain upper part 22 in the proper orientation with lower part 32 (and hence to prevent falling or pivoting of upper part 22). Similarly, where wedge portion 70 provides only a minor additional distracting force (which distracting force also serves to support or hold), this distracting force of wedge portion 70 will primarily be exerted at the anterior portion of upper part 22 to which upper arm 57 is directly attached. Typically when either no distracting force (with supporting/holding occurring) or some additional distracting force is exerted by wedge portion 70, wedge portion 70 only effects a supporting/holding and/or distracting force on the anterior part of upper part 22 as heads 64 of fork arms 63 travel further along the posterior half thereof; but this supporting/holding/forcing could occur starting at the beginning of the forward engaging movement of heads 64, but more likely will occur starting near the end of the forward movement of heads 64 (the end of the forward movement of distractor 60). In addition, wedge portion 70 can begin providing only a supporting/holding force and then provide some distracting force, or vice versa or alternately, as the forward movement of distractor 60 occurs.

While two relative extremes of the two distracting forces of heads 64 of fork arms 63 and of wedge portion 70 have been described above, in practice wedge portion 70 and heads 64 will be designed so that in many or even most situations it will be some, possibly changing, combination of the distracting forces of both heads 64 of fork arms 63 and wedge portion 70 which will effect the distracting movement of upper part 22 away from lower part 32. In general, however, as noted above, it is anticipated that where the separation space is more easily produced (a small separating force is needed), wedge portion 70 will do more of the separating while heads 64 act more as a support; while where the separation space is less easily produced (a larger separating force is needed), heads 64 will do more of the separating (and supporting) while wedge portion 70 does less.

Figure 12:
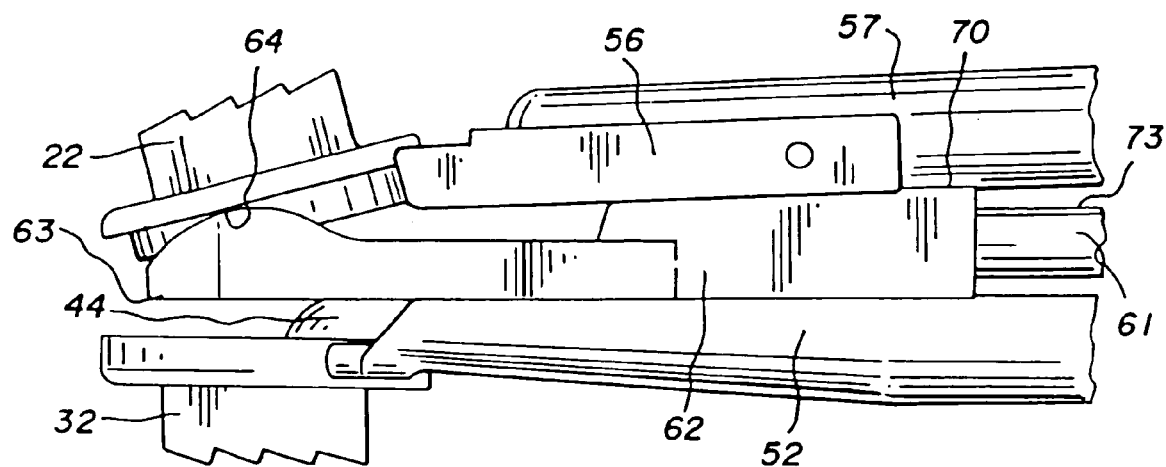
FIG. 12 is a side elevational view of a modified fork distractor of the present invention supporting the upper part of an intervertebral disc implant as the pivot element is being inserted into the space between the upper and lower parts.

It will be appreciated that the force of heads 64 of fork arms 63 acts between lower arms 52, 53 on which body 62 rests and the engaging portions of heads 64 of fork arms 63 on the lower/inner surface of upper part 22 as shown in FIGS. 10-12. As the attachment of lower part 32 to lower arms 52 is strong (relative to the attachment of upper part 22 to upper arm 57), there is no problem with lower part 32 moving relative to lower arms 52. And as the reactive force of heads 64 of the fork arms 63 is on the surface of upper part 22, this force acts directly to hold/force upper part 22 away from lower part 32.

Where the reactive force of heads 64 of fork arms 63 does begin at the anterior end of the facing/inner surface of upper part 22, this force moves forward along this surface with only a small distracting force until heads 64 are moved substantially inward (forward) to the posterior portion as shown in FIGS. 10 and 12. Preferably, the distracting force of heads 64 begin at about the midway point between the anterior and posterior ends of the surfaces. In this way, there is a more forceful pivoting torque exerted by heads 64 of fork arms 63 on the surface of upper part 22 as fork arms 63 advance further (as the moment arm length increases, as the moment arm length is measured from the forward end of U-shaped holder 56). This is advantageous since generally it is desired to have more separating torque or force at the posterior end of upper part 22 where a greater resistance to separation is expected.

In addition, it will be appreciated that arm 61 of distractor 60 has a stop pin 75 (FIG. 4) which engages a casing 66 to signify when distractor 61 is fully inserted. In particular, pin 75 is thus specifically positioned on arm 61 to engage casing 66 at the point where heads 64 of fork arms 63 have advanced fully or forwards sufficiently into the space between upper part 22 and lower part 32 to provide the needed spacing for the completion of the insertion of pivot element 42 (and clearance for inlay protrusion 44) by the action of pushing element 80 (FIG. 10). At this fully inserted position, heads 64 of fork arms 63 are at a maximum distance from the anterior end of upper part 22 so that a maximum pivoting torque can be exerted by heads 64 (as noted above, where the moment arm is greatest) in case the forces resisting distraction are at their highest (at the maximum displacement of upper part 22 and lower part 32, which is the maximum vertebral spacing).

FIG. 11 clearly shows the relationship between distractor 60 and, as shown in the drawing, the lower/inner surface of upper part 22, wherein fork arms 63 flank domed-shaped bearing face 26. This positioning allows pivot element 42 (not shown in FIG. 11) to be pushed partially into position in recess 35 as heads 64 of fork arms 63 are moved forward to support upper part 22 in the raised position (where pusher element 80, without interference with distractor 60, then completes pushing pivot element 42 into recess 35 as previously noted).

Figure 13A:
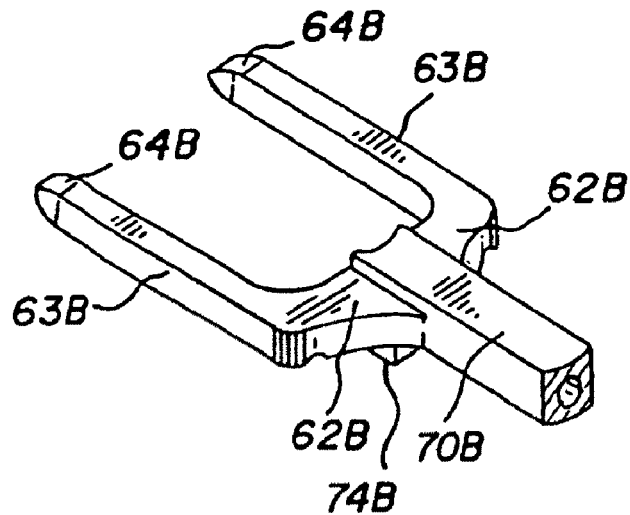
FIG. 13A is a perspective view of modified forked arm in accordance with the present invention and FIG. 13B is a perspective view of the forked arms shown in FIG. 12.
Figure 13B:
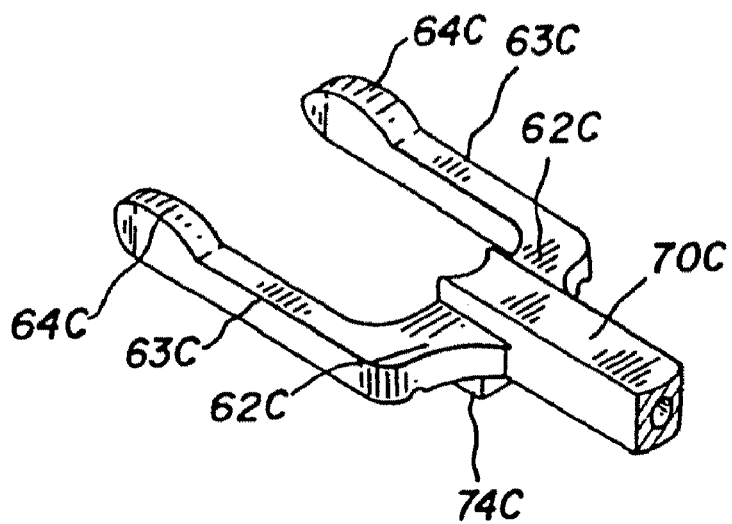

FIGS. 13A and 13B show different bodies 62B and 62C with protrusions 74B and 74C and fork arms 63B and 63C that may be used in connection with distractor 60 of the present invention. Obviously, the different vertical thicknesses or heights of heads 64B and 64C of respective fork arms 63B and 63C provide for the creation of different height insertion spaces between upper part 22 and lower part 32, which would correspond to the different available heights of protrusions 44 (FIG. 2) typically provided in a set of pivot elements 42. In addition, it will be noted that wedge portions 70B and 70C are respectively vertically thicker or higher in correspondence with the increased thickness of heads 64B and 64C of fork arms 63B and 63C. This corresponding thickness is needed to maintain the proper orientation of upper part 22 to lower part 32 during use of distractor 60. However, if desired or needed, the heights of heads 64B and 64C could be lowered or raised to effect lesser or greater holding/distracting forces by heads 64B and 64C relative to wedge portions 70B and 70C; and similarly but probably less preferably, the heights of wedge portions 70B and 70C could be lowered or raised to effect lesser or greater holding/distracting forces by wedge portions 70B and 70C relative to heads 64B and 64C.

As noted above, and referring to FIGS. 3 and 4, portion 66A secures distractor 60 to mounting structure 54 via opening 54A and the ball catch therein in the much the same manner as the distractor is attached in WO 01/19295. As shown in FIG. 4, distractor 60 further comprises a hex end 67 which extends rotatably through casing 66 and beyond mounting portion 66A and which is designed to be engaged by a suitable wrench having a mating hex socket or the like (not shown) if desired. However, in this preferred embodiment, the opposite end from hex end 67 is provided with a square end or the like (not shown) to which is securely mounted a thumbscrew 69. Turning of either thumbscrew 69 or hex end 67 results in the turning of a gear wheel (not shown, but inside casing 66) which engages a tooth rack 65 on elongated arm 61. This system may be used to carefully and precisely advance distractor 60 longitudinally Forward towards the second ends of arms 52, 53 and 57 as noted above and in much the same manner as the distractor is advanced in WO 01/19295—except that a more positive and forceful insertion force can be exerted on tooth rack 65 by the use of the wrench if such insertion force is needed. As noted above, portion 66A secures distractor 60 to mounting structure 54 via opening 54A and the ball catch therein in the much the same manner as the distractor is attached in WO 01/19295. As shown in FIG. 4, distractor 60 further comprises a hex end 67 which extends rotatably through casing 66 and beyond mounting portion 66A and which is designed to be engaged by a suitable wrench having a mating hex socket or the like (not shown) if desired. However, in this preferred embodiment, the opposite end from hex end 67 is provided with a square end or the like (not shown) to which is securely mounted a thumbscrew 69. Turning of either thumbscrew 69 or hex end 67 results in the turning of a gear wheel (not shown, but inside casing 66) which engages a tooth rack 65 on elongated arm 61. This system may be used to carefully and precisely advance distractor 60 longitudinally Forward towards the second ends of arms 52, 53 and 57 as noted above and in much the same manner as the distractor is advanced in WO 01/19295—except that a more positive and forceful insertion force can be exerted on tooth rack 65 by the use of the wrench if such insertion force is needed.

The insertion instrument described herein comprises a biocompatible metal, such as titanium or a titanium alloy or a stainless steel composite; and may be the same or different material as the upper and lower parts. Pivot element 42 is also made from a biocompatible material, and is preferably a biocompatible plastic material such as polyethylene. Furthermore, distractor 60 may comprise a biocompatible coating that assists sliding relative to the arms, or distractor 60 may comprise a plastic material for the same reason.

Figure 5:
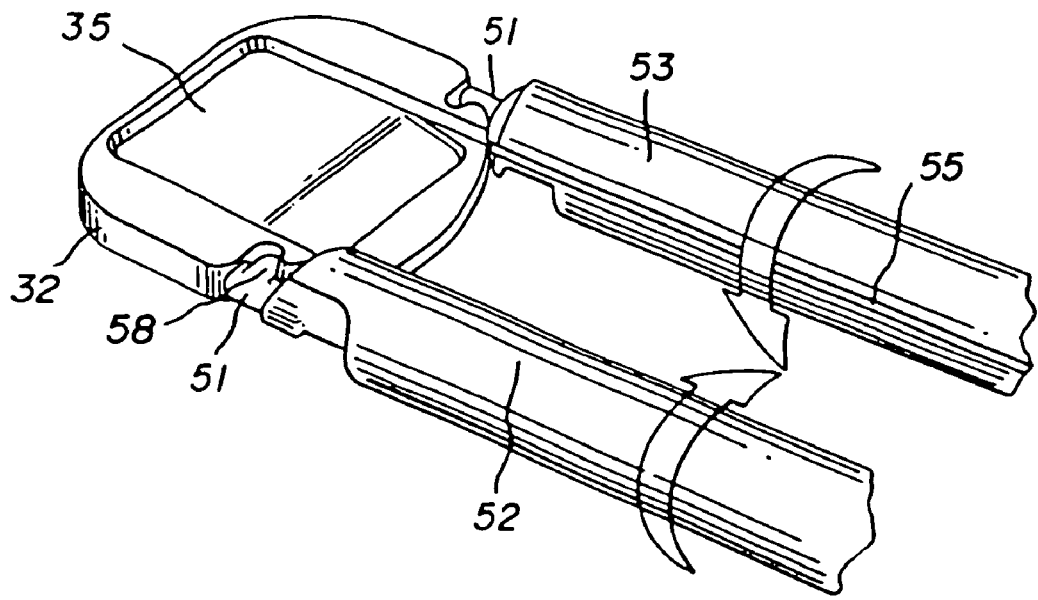
FIG. 5 is a perspective view of the lower arms engaging the lower part of an intervertebral disc implant.
Figure 6:
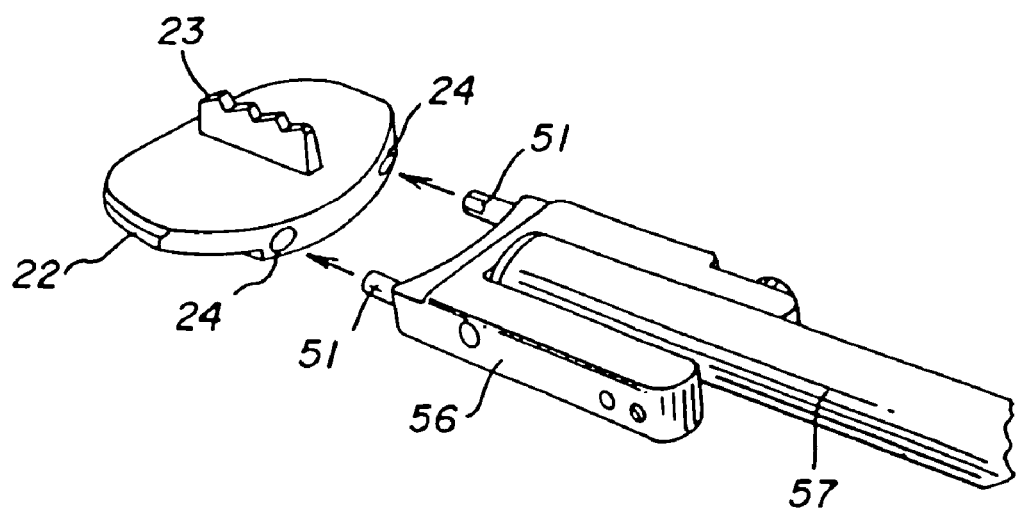
FIG. 6 is a perspective view of the upper arm engaging the upper part of the intervertebral disc implant.

Thus, in operation and after suitable preparation as described above and as known in the art, upper part 22 and lower part 32 are engaged with upper arm 57 and lower arms 52, 53 as shown in FIGS. 5 and 6. Lower part 32 is locked to lower arms 52, 53 by rotation thereof, which causes locking bar protrusions 58 to engage recesses 36 of lower part 32. Upper and lower parts 22, 32 are then brought to their closest proximity, preferably nested together (as no pivot element is yet present), and inserted into the intervertebral space as shown in FIG. 8.

Figure 9:
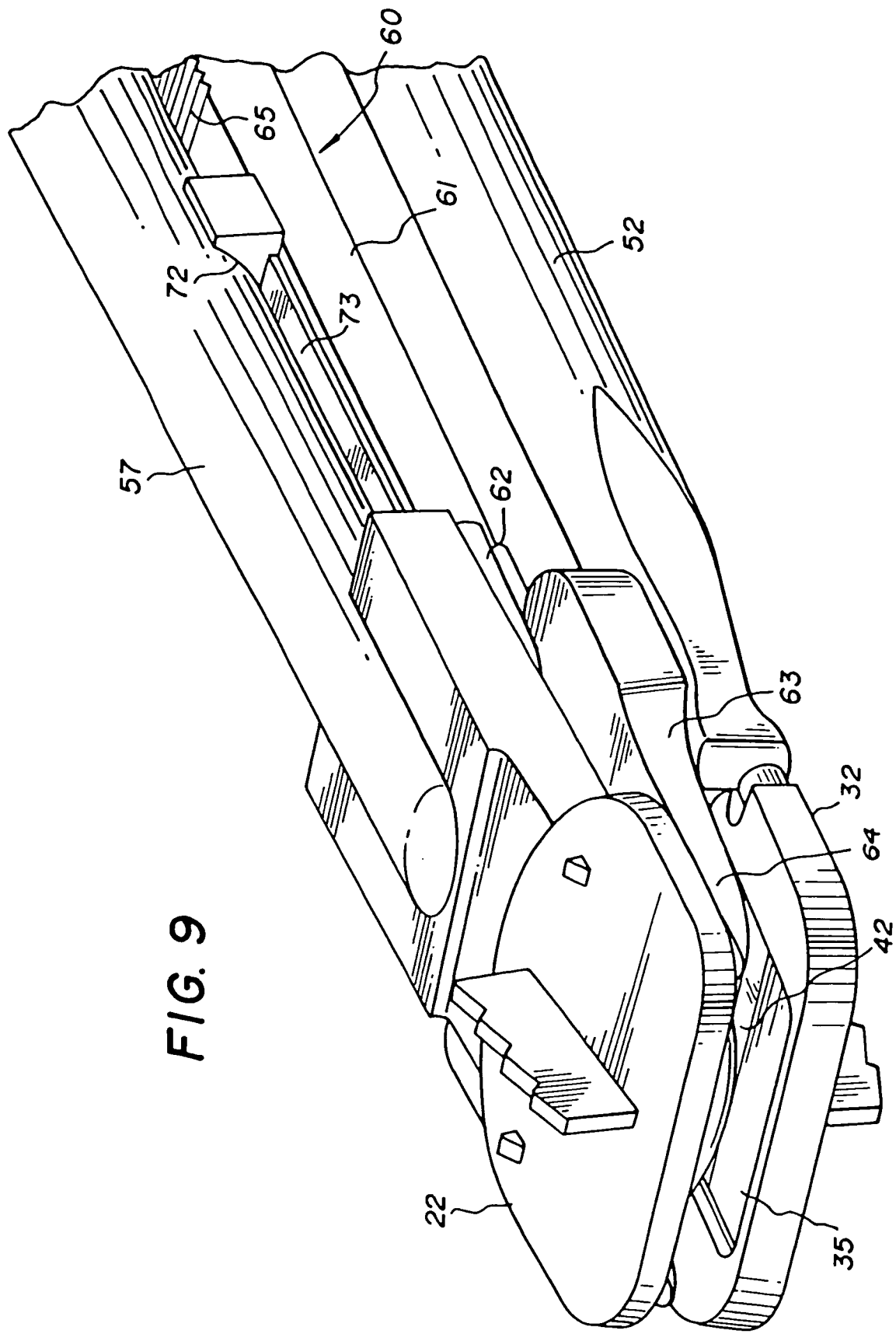
FIG. 9 is a front, top and side perspective view of an insertion instrument of the present invention creating an introduction space for the pivot element of an intervertebral disc implant.

After insertion of upper and lower parts 22, 32 forwardly into the intervertebral space, pivot element 42 is inserted between lower arms 52 adjacent the rear thereof. After mounting of distractor 60, pivot element 42 is then moved forward towards the intervertebral space by distractor 60 with edges 45 thereof engaging grooves 55 formed in lower arms 52, 53 as described in WO 01/19295. As shown in FIGS. 9, 10 and 12, once the starting space is created, further forward advancement of wedge portion 70 causes heads 64 of fork arms 63 to engage the bottom/inner surface of upper part 22 as noted in detail above, pushing and/or holding upper part 22 away from lower part 32 which is held in place by lower arms 52, 53. With the advancement of arm 61, the space between upper part 22 and lower part 32 is made large enough to accommodate the similar advancement of pivot element 42 into lower part 32. In the final step, pusher element 80 is used to complete the insertion of pivot element 42 into locked engagement with recess 35 of lower part 32 as described in WO 01/19295.

Following insertion of pivot element 42, pusher element 80 and distractor 60 are retracted and upper part 22 and lower part 32 are permitted to come together under the force of the adjacent vertebrae which have been displaced, until all parts of intervertebral disc implant 21 engage one another and attain their final position (as shown in FIG. 1). Finally, by rotation of lower arms 52, 53 about their longitudinal axes, the engagement of locking bar protrusions 58 is undone and insertion instrument 50 can be pulled rearwardly off the now properly inserted and completed intervertebral implant 21.

Figure 14:
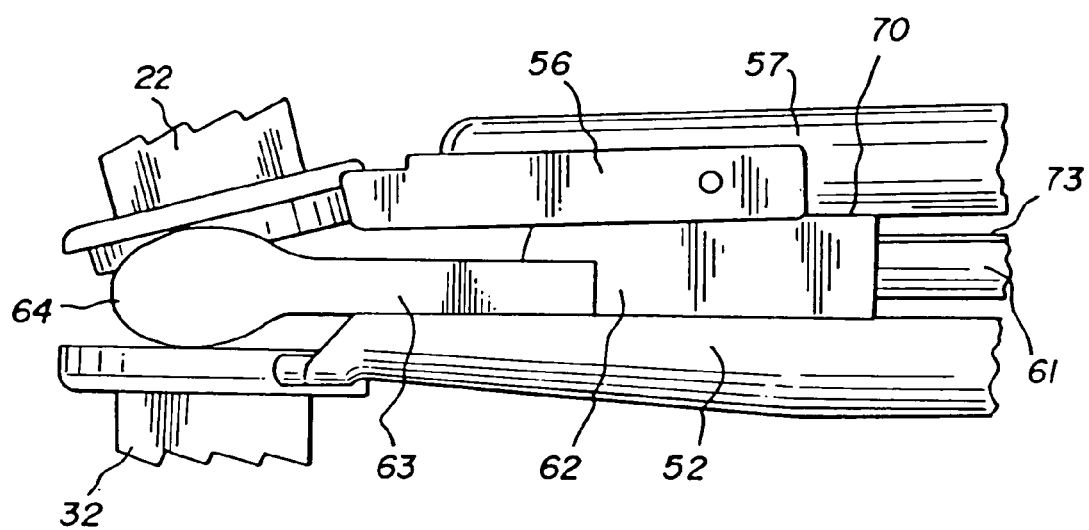
FIG. 14 is a side elevational view of an alternative fork distractor of the present invention where the fork arms are supporting both the upper part and lower part as the pivot element is being inserted therebetween.

While heads 64 of fork arms 63 have been described above as only engaging the lower/inner surface of upper part 22 as fork arms 63 advance into the intervertebral space provided between upper part 22 and lower part 32, it will be appreciated that engagement of the upper surface of lower part 32 would be possible as shown in FIG. 14. Thus, a more positive separation of upper part 22 from lower part 32 using heads 64 would be achieved as the separating force would be directly exerted between the facing surfaces of lower part 32 and upper part 22 by heads 64 of fork arms 63 once heads 64 of fork arms 63 completely entered the space provided between upper part 22 and lower part 32. The holding forces of arms 52, 53 and 57 on upper part 22 and lower part 32 in this embodiment would thus not need to be as secure.

Although the invention has been described in considerable detail with respect to preferred embodiments, it will be apparent that the invention is capable of numerous modifications and variations, apparent to those skilled in the art, without departing from the spirit and scope of the claims.

We claim:

1. An insertion instrument for inserting an intervertebral implant of the type having an upper part and a lower part with facing surfaces which face each other, comprising:
    an upper arm and a lower arm disposed adjacent each other and pivotally supported relative to one another at respective held ends thereof, each upper and lower arm having a free end for engaging with an associated one of the upper and lower parts of the implant; and
    a distractor which engages the arms, moves along the arms, and separates the free ends of the upper and lower arms and hence the upper and lower parts from each other, the distractor including
        a body having seats which engage the arms and whose movement along the arms causes the separation of the free ends, and
        said seats having a distal end, a forward arm protruding forwardly from said distal end for engaging one of the facing surfaces of the upper and lower parts as the upper and lower parts are forced apart; and
    wherein the lower arm comprises a pair of elongated arms disposed substantially parallel to each other, and the distractor is positioned for guided movement along the elongated arms and the upper arm;
    wherein the body comprises a groove shaped wedge portion shaped to slidably engage the upper arm as the wedge portion approaches the implant; and
    wherein the elongated arms form between them a receiving chamber, the body of the distractor rests on the elongated arms and has a protrusion that extends down between the elongated arms into the receiving chamber, and the body further includes a resilient element which engages the upper arm when the body is adjacent the held ends of the upper and elongated arms to maintain the body resting on the elongated arms as the body is advanced toward the implant.

2. The insertion instrument as claimed in claim 1, wherein the resilient element is a leaf spring attached to the body and having a seat which slidingly engages the upper arm.

3. The insertion instrument as claimed in claim 1, wherein the forward arm comprises a pair of fork arms.

4. The insertion instrument as claimed in claim 3, wherein each forked arm includes a tapered head.

5. The insertion instrument as claimed in claim 4, wherein each head includes a surface which engages and slides along the upper part.

6. The insertion instrument as claimed in claim 4, wherein each head includes opposed surfaces which engage and slide respectively along both the upper part and the lower part.

7. The insertion instrument as claimed in claim 1, wherein at least one of the upper and lower arms has a structure for mounting the distractor, and the distractor includes an elongated distractor arm connected to the body and movable relative to the structure to positively move the body toward the implant.

8. The insertion instrument as claimed in claim 7, wherein the distractor arm includes a stop which is engaged to prevent further movement of the body toward the implant when the distractor separates the upper and tower parts a predetermined distance.

9. The insertion instrument as claimed in claim 1, wherein the forward arm comprises a platform for engaging one of the upper or lower parts.

10. The insertion instrument as claimed in claim 1,
    wherein the body comprises a groove shaped wedge portion shaped to slidably engage the upper arm as the wedge portion approaches the implant; and
    wherein the forward arm comprises a pair of fork arms, each fork arm having a respective head which slidably engages the one of the facing surfaces.

11. The insertion instrument as claimed in claim 10, wherein the wedge portion effects a majority of a distracting force which separates the upper and lower parts as the wedge portion moves along the arms, and wherein the heads effect at least a supporting force on the one of the facing surfaces as the distracting force is effected.

12. The insertion instrument as claimed in claim 10, wherein the heads effect a majority of a distracting force which separates the upper and lower parts as the heads move along the one of the facing surfaces, and wherein the wedge portion effects at least a supporting force on the upper and lower parts as the distracting force is effected.

13. In combination, an instrument for inserting an intervertebral implant into an intervertebral space, the combination comprising:
    an implant comprising an upper part and a lower part having facing surfaces which face each other; and
    an implant insertion instrument comprising an upper arm for engaging the upper part, lower arms pivotally connectable to the upper arm and engaging the lower part, and a distractor between the upper and lower arms having seat portions which engage the arms and which are moved toward the upper and lower parts for separating the upper arm from the lower arm and hence for separating the upper part and the lower part;
    wherein the distractor creates a starting space between the upper part and the lower part and the distractor has a forward arm which protrudes forwardly of the seats and which is constructed and positioned to enter the starting space and to engage and move along at least one of the facing surfaces of the upper and lower parts for at least maintaining a separation of the upper and lower parts during use;
wherein the distractor comprises a body with a wedge portion to slidably receive the upper arm to create the starting space, the wedge including a first one of the seats;
wherein the forward arm comprises a plurality of parallel fork arms; and
wherein the body further includes a resilient seat which engages and moves along the upper arm to maintain the body in position between the lower arms.

14. The combination of claim 13
further comprising a third part disposable between the upper and lower parts;
wherein the lower arms each have a corresponding longitudinal guide structure to engage the third part for sliding movement therealong toward and into the implant; and
wherein the body of the distractor further includes a protrusion which engages the third part as the fork arms are moved toward the upper and lower parts to move the third part into position between the separated upper and lower parts.

15. The combination of claim 13, wherein each fork arm has a leading head.

16. The combination as claimed in claim 15, wherein each head includes opposed surfaces which engage and slide respectively along both the upper part and the lower part.

17. The combination of claim 15, further including a structure which mounts the lower arms pivotally to the upper arm; and wherein the distractor includes an elongated distractor arm connected to the body and actuatable relative to the structure to positively move the body toward the implant.

18. The combination of claim 17, wherein the distractor arm includes a stop which is engaged by the implant to prevent further movement of the body toward the implant when the forward arm has further separated the upper and lower parts a predetermined distance.

19. The combination of claim 13, wherein the distractor comprises a body with the seats, the seats being surfaces for engaging the lower arms and a wedge portion for engaging the upper arm.

20. The combination as claimed in claim 13, wherein the wedge portion effects a majority of a distracting force which separates the upper and lower parts as the wedge portion moves along the arms, and wherein the forward arm effects at least a supporting force on the one of the facing surfaces as the distracting force is effected.

21. The combination as claimed in claim 13, wherein the forward arm effects a majority of a distracting force which separates the upper and lower parts as the forward end moves along the one of the facing surfaces, and wherein the wedge portion effects at least a supporting force on the upper and lower parts as the distracting force is effected.

22. A method for inserting an intervertebral implant into an intervertebral space, comprising the steps of:
assembling upper and lower parts of the intervertebral implant together on respective upper and lower arms of an elongated inserting instrument such that the upper and lower parts have facing surfaces which face each other;
inserting the upper and lower parts into an intervertebral space such that an upper surface of the upper part and a lower surface of the lower part engage adjacent vertebrae;
after the upper part and lower part are located in the intervertebral space, separating the upper and lower parts from each other with the elongated inserting instrument, wherein the separating step includes
to initially separate the upper and lower parts apart, moving a distractor having contacting seats along upper and lower arms, which arms respectively engage the upper and lower parts, toward the upper and lower parts such that the distractor movement initially moves one of the upper and lower parts in the intervertebral space away from the other,
engaging a portion of the distractor extending forwardly of the seats with one of the facing surfaces of the upper and lower parts as the upper and lower parts separate, and
when the upper and lower parts are separated, inserting a third part of the implant into a space between the upper and lower parts created by the separating step while the elongated inserting instrument engages and supports the one of the facing surfaces; and
wherein said engaging step includes the providing of a pair of fork arms as the portion of the inserting instrument engage the one of the facing surfaces;
wherein said inserting step includes the moving of the third part with the distractor;
wherein the distractor includes a body which moves along an upper arm and a pair of lower arms of the instrument, the body including a protrusion which engages the third part which is also mounted for movement along the lower arms;
wherein said inserting step includes the moving of the third part with the protrusion; and
wherein said separating step includes providing the body with a wedge portion including a first one of the seats which forces the upper arm away from the lower arm as the body moves, and providing the body with a resilient mounting to the upper arm to keep the body in position on the lower arms.

23. The method for inserting of claim 22, wherein said engaging step includes the providing of a tapered head on each fork arm.

24. The method for inserting of claim 22, wherein said engaging step includes the engaging of each fork arm with both facing surfaces of the upper and lower parts.

25. The method for inserting of claim 22, wherein said engaging step includes moving the body by a force exerted on an elongated member until a stop on the member engages an associated part of the instrument.

26. The method for inserting of claim 22, wherein the distractor movement effects a majority of a distracting force which separates the upper and lower parts as the distractor moves along the arms, and wherein the portion of the inserting instrument effects at least a supporting force on the one of the facing surfaces as the distracting force is effected.

27. The method for inserting of claim 22, wherein the portion of the inserting instrument effects a majority of a distracting force which separates the upper and lower parts as the portion of the inserting instrument moves along the one of the facing surfaces, and wherein the distractor movement effects at least a supporting force on the upper and lower parts as the distracting force is effected.

28. An insertion instrument for inserting an intervertebral implant of the type having an upper part and a lower part with facing surfaces which face each other, comprising:
an upper arm and a lower arm disposed adjacent each other and pivotally supported relative to one another at respective held ends thereof, each upper and lower arm having a free end which is engageable with an associated one of the upper and lower parts of the implant; and a distractor which rests on the arms, moves along the arms, and separates the free ends of the upper and lower arms and hence the upper and lower parts from each other, the distractor including a body having a distal end and a forward arm protruding forwardly from said distal end, wherein the forward end engages one of the facing surfaces of the upper and lower parts as the upper and lower parts are forced apart, and wherein the body includes a resilient element which engages the upper arm to maintain the body resting on the lower arms as the body is advanced toward the implant.

29. The insertion instrument as claimed in claim 28, wherein the resilient element is a leaf spring attached to the body and having a seat which slidingly engages the upper arm.

30. The insertion instrument as claimed in claim 28, wherein the lower arms form between them a receiving chamber, and wherein the body of the distractor has a protrusion that extends down between the lower arms into the receiving chamber.

31. The insertion instrument as claimed in claim 28, wherein the forward arm of the distractor comprises a pair of fork arms.

32. The insertion instrument as claimed in claim 31, wherein each forked arm includes a tapered head.

33. The insertion instrument as claimed in claim 32, wherein each head includes a surface which engages and slides along the upper part.

34. The insertion instrument as claimed in claim 32, wherein each head includes opposed surfaces which engage and slide respectively along both the upper part and the lower part.

* * * * *